United States Patent
Rodenbostel et al.

(10) Patent No.: US 11,445,844 B2
(45) Date of Patent: Sep. 20, 2022

(54) PROSTHETIC LOCKING LINER DRYING HOOK

(71) Applicants: Claus Peter Rodenbostel, Apollo Beach, FL (US); Deborah Diana Rodenbostel, Apollo Beach, FL (US)

(72) Inventors: Claus Peter Rodenbostel, Apollo Beach, FL (US); Deborah Diana Rodenbostel, Apollo Beach, FL (US)

( * ) Notice: Subject to any disclaimer, the term of this patent is extended or adjusted under 35 U.S.C. 154(b) by 44 days.

Patent file contains an affidavit/declaration under 37 CFR 1.130(b).

(21) Appl. No.: 16/931,042

(22) Filed: Jul. 16, 2020

(65) Prior Publication Data
US 2022/0015561 A1    Jan. 20, 2022

(51) Int. Cl.
| | |
|---|---|
| A47G 29/08 | (2006.01) |
| A47K 3/28 | (2006.01) |
| F16B 45/00 | (2006.01) |
| A61F 2/78 | (2006.01) |

(52) U.S. Cl.
CPC .......... *A47G 29/08* (2013.01); *A47K 3/281* (2013.01); *A61F 2/7812* (2013.01); *F16B 45/00* (2013.01)

(58) Field of Classification Search
CPC ....... A47G 29/08; A47K 3/281; A61F 2/7812; F16B 45/00
USPC .......................... 248/322, 339, 340, 341, 558
See application file for complete search history.

(56) References Cited

U.S. PATENT DOCUMENTS

| | | | | |
|---|---|---|---|---|
| 562,566 A | * | 6/1896 | Baynes | F16M 13/00 248/317 |
| 664,217 A | * | 12/1900 | Jencke et al. | B44D 3/123 248/692 |
| 2,927,701 A | * | 3/1960 | Lynde, Jr. | G09F 3/20 211/87.01 |
| 2,951,672 A | * | 9/1960 | Bott | B60N 3/12 248/317 |

(Continued)

FOREIGN PATENT DOCUMENTS

| | | | | |
|---|---|---|---|---|
| DE | 202005011836 U1 | * | 10/2005 | .............. F16B 45/00 |
| FR | 2676344 A1 | * | 11/1992 | ............... A47G 1/20 |

(Continued)

OTHER PUBLICATIONS https://www.youtube.com/watch?v=rUhc91vfxsg&t=4s, MY Liner Buddy, Jun. 22, 2020, Youtube, 1:11 minutes. (Year: 2020).*

(Continued)

*Primary Examiner* — Kimberly T Wood

(57) ABSTRACT

A prosthetic locking liner drying hook includes a bottom grip lever extending in a generally horizontal direction; a top grip lever connected to the bottom grip lever by a first curved connecting member extending from an edge of the top grip lever to an edge of the bottom grip lever; and at least one hole extending through each of the top grip lever and the bottom grip lever. A second curved connecting member connects the top grip member to the bottom grip lever. A vertically extending plate extends upwardly from the second curved member, and at least one curtain rod hook or shower door hook projecting from the vertically extending plate; wherein the prosthetic locking liner drying hook is configured to receive a prosthetic locking liner through a prosthetic liner pin extending through the top and bottom grip levers.

15 Claims, 10 Drawing Sheets

(56) References Cited

U.S. PATENT DOCUMENTS

| | | | | | |
|---|---|---|---|---|---|
| 3,015,177 | A * | 1/1962 | Hembd | G09F 1/10 | 40/665 |
| 3,052,004 | A * | 9/1962 | Wallshein | A61C 7/12 | 24/129 R |
| 3,253,813 | A * | 5/1966 | Schwab | A47G 25/1478 | 248/339 |
| 3,377,038 | A * | 4/1968 | Loudon | F16L 3/1207 | 248/59 |
| 3,415,473 | A * | 12/1968 | Ollen | F16L 3/133 | 248/59 |
| 3,792,804 | A * | 2/1974 | Ponzo | A47G 25/24 | 223/85 |
| 3,952,985 | A * | 4/1976 | Davenport | F21V 21/08 | 248/317 |
| 4,036,460 | A * | 7/1977 | Storck | F16L 3/133 | 248/59 |
| 4,245,806 | A * | 1/1981 | Vangreen | F16L 3/133 | 248/59 |
| 4,377,046 | A * | 3/1983 | Johnson | G09F 3/20 | 248/305 |
| 4,510,872 | A * | 4/1985 | Parry | B43M 99/00 | 108/25 |
| 4,524,936 | A * | 6/1985 | Hurtubise | F16L 3/221 | 248/62 |
| 4,749,160 | A * | 6/1988 | Shih | B25H 3/04 | 211/66 |
| 4,856,774 | A * | 8/1989 | Kowalcyk | A63B 21/0724 | 482/104 |
| 4,887,785 | A * | 12/1989 | Blaich | A01K 39/00 | 248/339 |
| 4,976,410 | A * | 12/1990 | Tomaiuolo | B60R 13/005 | 116/173 |
| 5,195,710 | A * | 3/1993 | Remblier | B23Q 1/5462 | 248/201 |
| 5,259,165 | A * | 11/1993 | Koyama | E04C 3/06 | 403/387 |
| 5,303,885 | A * | 4/1994 | Wade | F16L 3/133 | 24/543 |
| 5,312,079 | A * | 5/1994 | Little, Jr. | F21V 21/088 | 248/230.6 |
| 5,355,646 | A * | 10/1994 | Bischel | E04B 9/16 | 24/563 |
| 5,376,132 | A * | 12/1994 | Caspers | A61F 2/5046 | 264/222 |
| 5,758,465 | A * | 6/1998 | Logue | E04B 9/18 | 403/403 |
| 5,810,232 | A * | 9/1998 | Meurer | A45F 5/02 | 224/270 |
| 6,010,103 | A * | 1/2000 | Ashworth | B25C 7/00 | 173/171 |
| 6,517,032 | B1 * | 2/2003 | Gretz | F16L 3/133 | 248/62 |
| 6,581,884 | B1 * | 6/2003 | Gretz | F16L 3/133 | 24/278 |
| 7,201,355 | B1 * | 4/2007 | Zien | A01K 5/01 | 248/301 |
| 7,464,910 | B1 * | 12/2008 | St. Germain | G10G 5/00 | 211/85.6 |
| 7,641,356 | B2 * | 1/2010 | Pieroth | F21L 15/10 | 362/130 |
| 7,698,867 | B1 * | 4/2010 | Stucko | E04F 13/0864 | 52/548 |
| 8,157,235 | B2 * | 4/2012 | Quertelet | H02G 3/0443 | 248/339 |
| 8,672,281 | B2 * | 3/2014 | Ernst | E04B 9/18 | 248/327 |
| 8,857,771 | B2 * | 10/2014 | Streetman | F16L 3/133 | 248/72 |
| 9,188,152 | B1 * | 11/2015 | Kacines | A47G 25/00 | |
| 10,227,776 | B2 * | 3/2019 | Mayer | E04B 9/065 | |
| D882,381 | S * | 4/2020 | Bartos | D8/380 | |
| 11,111,677 | B2 * | 9/2021 | Kotiadis | E04F 13/007 | |
| 2003/0066938 | A1 * | 4/2003 | Zimmerman | F21V 21/088 | 248/301 |
| 2004/0149877 | A1 * | 8/2004 | Herrmann | B05B 15/62 | 248/312 |
| 2005/0056736 | A1 * | 3/2005 | Thompson | F16L 3/133 | 248/58 |
| 2006/0289373 | A1 * | 12/2006 | Kahn | B63B 32/80 | 211/85.7 |
| 2010/0198361 | A1 * | 8/2010 | Warila | A61F 2/80 | 623/33 |
| 2011/0042528 | A1 * | 2/2011 | Tucker | F16L 3/133 | 248/62 |
| 2014/0306082 | A1 * | 10/2014 | Harvala | A47G 25/743 | 248/339 |
| 2015/0306447 | A1 * | 10/2015 | Neal-Buhler | A63B 21/0557 | 248/231.81 |

FOREIGN PATENT DOCUMENTS

| | | | | |
|---|---|---|---|---|
| FR | 2731052 A1 * | 8/1996 | | F16B 45/00 |
| GB | 2083857 A * | 3/1982 | | F16B 2/12 |

OTHER PUBLICATIONS https://www.mylinerbuddy.com/pages/the-my-liner-buddy, MY Liner Buddy, Jun. 22, 2020, p. 1 (Year: 2020).*

* cited by examiner

PROSTHETIC LOCKING LINER DRYING HOOK

CROSS REFERENCE TO OTHER APPLICATIONS

None

FEDERALLY SPONSORED RESEARCH

None

BACKGROUND OF THE INVENTION

Field of the Invention

The present disclosure relates to the prosthetic industry, and specifically to aiding the proper drying of prosthetic locking liners for amputees.

DESCRIPTION OF THE RELATED ART

In the amputee industry, a prosthetic liner is a protective cover worn over a residual limb. It is made from a flexible cushioning material, which reduces chafing, as well as movement between the socket and the skin of the amputee. Liners are the best available means of reducing bone pressure, preventing skin abrasions while wearing the prosthesis, and improving socket suspension for amputees.

Throughout the day, while worn by an amputee, prosthetic liners accumulate dirt, oil and bacteria that can lead to uncomfortable skin disorders if left alone and untreated; not to mention bad odors. Regular daily cleaning anything that will touch your skin is an easy and effective way to keep your limb healthy.

Many amputees clean a prosthetic locking liner and let the liner "air-dry" in the "inside-out" position. This causes the gel or silicone inside the liner to crack and deteriorate, which may void the manufactures warranty.

Currently available on the market are prosthetic liner hooks manufactured/sold by Able Prosthetic Care, Inc. Their website is https://linerhook.com. Another prosthetic liner hook is manufactured/sold by Bulldog Tools. Their website is:
http:/www.bulldogtools.com/prosthetic/advanced _search_result.php?keywords=hook&search. Review of the two companies's liner hooks shows both products to be structurally distinct from the instant invention. In addition, currently available on the market are prosthetic liner drying stands that are also distinct from the instant invention. The stands are manufactured/sold by Ottobock Company, which can be found on the
website: hdps://shop.ottobock.us/Prosthetics/Lower-Limb-Prosthetics/Socket-Technologies-Liners/Liner-Drying-Stand-for-TF-Liners/p/SY100-52, and by SPSCO Company which can be round on the website: https://www.spsco.com/product-type/prosthetics/accessories/alpha-liner-drying-stand. html.

SUMMARY OF THE INVENTION

The invention, as set forth in the appended claims, overcomes the above-described problems in the related art by providing a simple, ergonomic, and useful, one-piece, no assembly required, prosthetic locking liner dryer hook that allows a cleaned prosthetic locking liner to be dried in a proper position, which is to make sure that the liner is not drying inverted or in the inside-out and does not have wrinkles. Allowing the liner to dry inverted or in the inside-out position will cause the liner's interior gel or silicone to deteriorate and crack over time. By using the prosthetic locking liner drying hook of the present invention, the liner properly ventilates and dries in the correct position. Allowing the liner to hang dry in the proper position, meaning the liner fabric facing towards the outside and the gel or silicone facing on the inside, helps reduce both external and internal liner wrinkling and maintains proper form and fit for the patient's residual limb and avoids skin irritation by having the interior gel or silicones of the liner as smooth as possible.

One can either hang the prosthetic locking liner dryer hook on a shower curtain rod hook located on the anterior side of the hook or onto an integrated clasp construction for a shower door (up to 10 mm thick shower door) on the posterior side of the hook. One can also hang the prosthetic locking liner hook from any appropriate surface edge as well. Once the prosthetic locking liner has been cleaned, just squeeze the plastic grips on the prosthetic locking liner hook and insert the prosthetic liner pin, that is attached to a prosthetic locking liner to hold in place, and release, creating tension. The prosthetic locking liner will stay in position and is ready to be hung up and let dry. This will help with the longevity and life of the prosthetic locking liner and help air out, ventilate, and dry the prosthetic locking liner. An exemplary embodiment provides for a prosthetic locking liner drying hook which includes a bottom grip lever extending in a generally horizontal direction; a top grip lever connected to the bottom grip lever by a first curved connecting member extending from an edge of the top grip lever to an edge of the bottom grip lever; and at least one hole extending through each of the top grip lever and the bottom grip lever. A second curved connecting member connects the top grip lever to the bottom grip lever. A vertically extending plate extends upwardly from the second curved member, and at least one curtain rod hook and/or shower door hook projecting from the vertically extending plate; wherein the prosthetic locking liner drying hook is configured to receive a prosthetic locking liner through a prosthetic liner pin extending through the top and bottom grip levers.

REFERENCE NUMERALS

110—Curtain rod hook
112—Shower door hook
114—Top grip lever
116—Bottom grip lever
118—Vertical bar 120—Large hole for larger and thicker liner pins on the top grip lever
122—Small hole for small and thinner liner pins can the top grip lever
124—Large hole for larger and thicker liner pins on bottom grip lever
126—Smaller hole for smaller and thinner liner pins on bottom grip lever
128—1 mm reinforced interior plastic hole openings on top and bottom grip levers
130—Example of prosthetic liner pin
131—Bend in top grip lever 114 connecting to vertical bar 118
132—Example of prosthetic locking liner
137—Bend between top and bottom grip levers

DETAILED DESCRIPTION OF THE EXEMPLARY EMBODIMENTS

The prosthetic locking liner dryer hook is designed as a one-piece unit that is multifunctional, helpful, and an easy way to facilitate with the proper cleaning and handling of prosthetic locking liners. The levers are specially designed for the ease of use for one-hand operation that can be used by a child to a geriatric individual. The proper cleaning and handling of prosthetic locking liners is very crucial. Not only does proper cleaning and handling aid with the sanitary condition, longevity and life of a liner, but also with keeping the amputee's residual limb in a healthy fashion. The prosthetic locking liner dryer hook also helps amputees not void manufactures warranties of prosthetic liners. Prosthetic liners are cleaned both on the outside and the on the inside. But many times, they are left in the "inside-out" position to ventilate and air dry. Allowing the liners to dry in the "inside-out" or inverted position is very bad for the liner. Continuous and repetitiveness of these actions allowing the liner to be dried in the "inside-out" or an inverted fashion, will cause the gel or silicone inside of a liner to deteriorate, crack, and decompose. Prosthetic liners are not designed to be dried in the "inside-out" or inverted position and may result in the voiding of manufacturer's warranty. By using the prosthetic liner hook of the instant invention, once the prosthetic liner is cleaned, one can simply squeeze the plastic levers of the prosthetic locking liner dryer hook and insert the prosthetic locking liner pin in the proper size hole, release the plastic levers, and the liner will stay in place. The prosthetic locking liner hook is plastic in the preferred embodiment described in the patent application. While plastic is the preferred material, the prosthetic locking liner dryer hook can be made of polymers, metal, wood, etc. or combinations thereof, as would be understood by one of ordinary skill in the art. The prosthetic locking liner dryer hook designed to aid the drying of a prosthetic locking liner and have the choice of a shower curtain rod, a shower door, or an appropriate surface edge to let air-dry and ventilate.

Figure 1:
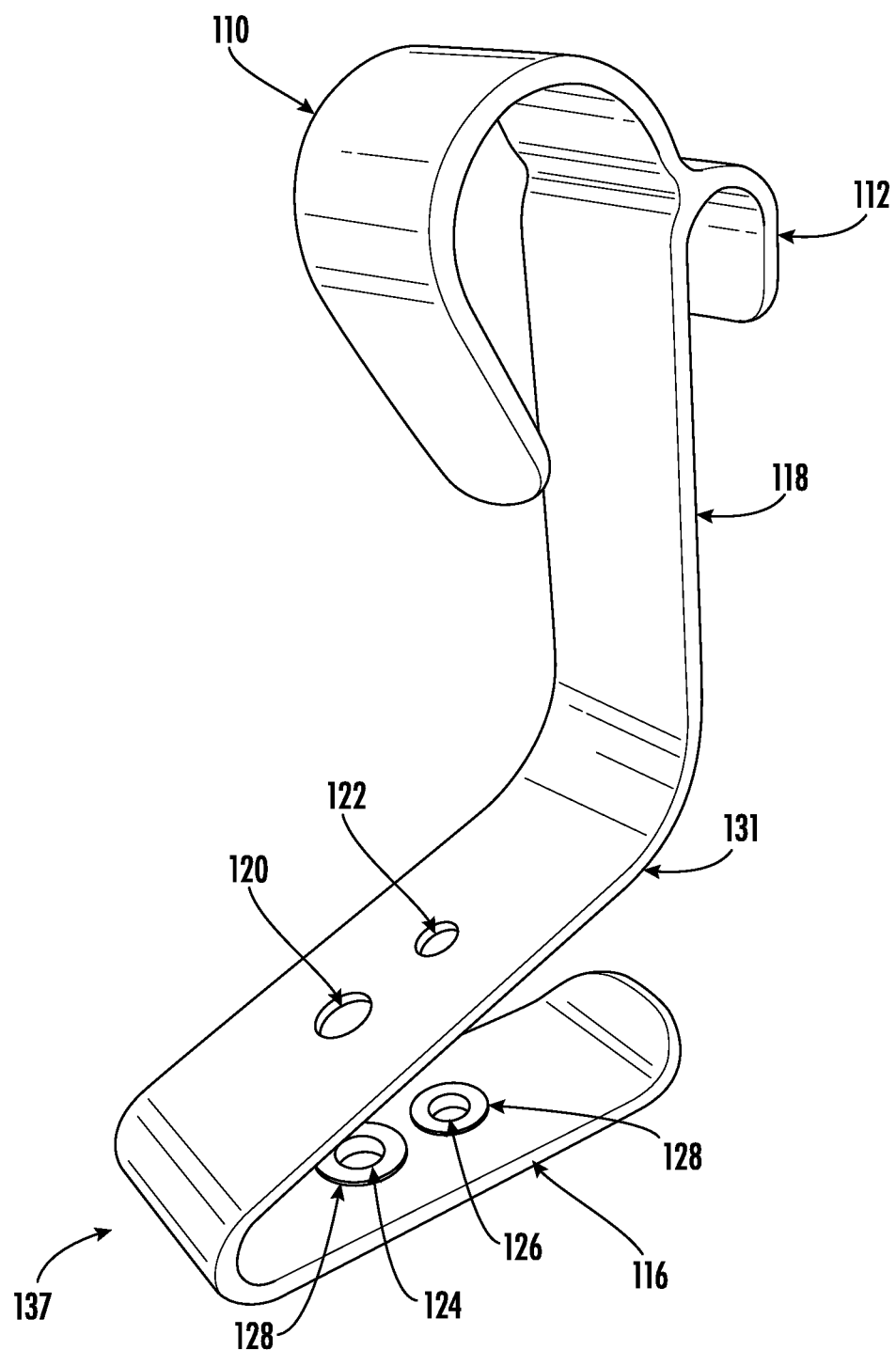
FIG. 1 is a perspective view of the invention

Turning to FIG. 1, a perspective view of an exemplary embodiment is illustrated. As shown in FIG. 1, a bottom grip lever 116 is illustrated. The structure of the bottom grip lever is that it is flat or substantially flat with a large opening 124 and a smaller opening 126, which are provided therein. At an edge of the bottom grip lever is a bend 137 which rises upwardly at an angle of about 25-40 degrees from the bottom grip lever to form a top grip lever 114. Although about 25-40 degrees angle is illustrated, larger or smaller degrees of angle or much larger or much smaller degrees of angles may be used, as would be readily understood by one of ordinary skill in the art. The top grip lever has a large opening 120 and a small opening 122. Although two holes are illustrated, more holes for larger and/or smaller pins may be used. In addition, on the underside of top grip lever are openings 120 and 122 which are 1 mm reinforced interior plastic hole openings, as illustrated in the drawings. Although 1 mm reinforced interior plastic hole openings are shown, the reinforcements can be larger, such as 4 mm or larger, or less than 1 mm, as would be understood by one of ordinary skill in the art. In addition, while the reinforcements 128 are illustrated as being of the same material as the prosthetic locking liner dryer hook, the reinforcements can be made of different materials, including metal, wood, polymers, etc, or combinations thereof. Each of the reinforcements can be different sizes. In addition, it is understood that reinforcements can be on either or both of the top and bottom levers. Although top and bottom levers are shown and illustrated, the invention my contain only the top lever which is at an angle and can carry the pin without a bottom lever; or the invention may contain only a bottom lever which is flat or substantially flat or angled but can hold the pin with reinforcements or a nut, or similar connector on the pin. At a top of top grip lever 114 is a curved surface 131 which bends upwardly, and is attached to a vertical bar 118. At the top of vertical bar 118 is a curtain rod hook 110 which extends in the general direction of bend 137. On the opposite side of the top of plate 118 is a shower door hook 112 which extends in the opposite direction of curtain rod hook 110. In addition, on the top surface of lower grip lever 116 are 1 mm reinforced interior plastic hole openings 128, which reinforce foe large and small holes 124 and 126, respectively, which receive prosthetic liner pins 130.

Figure 2:
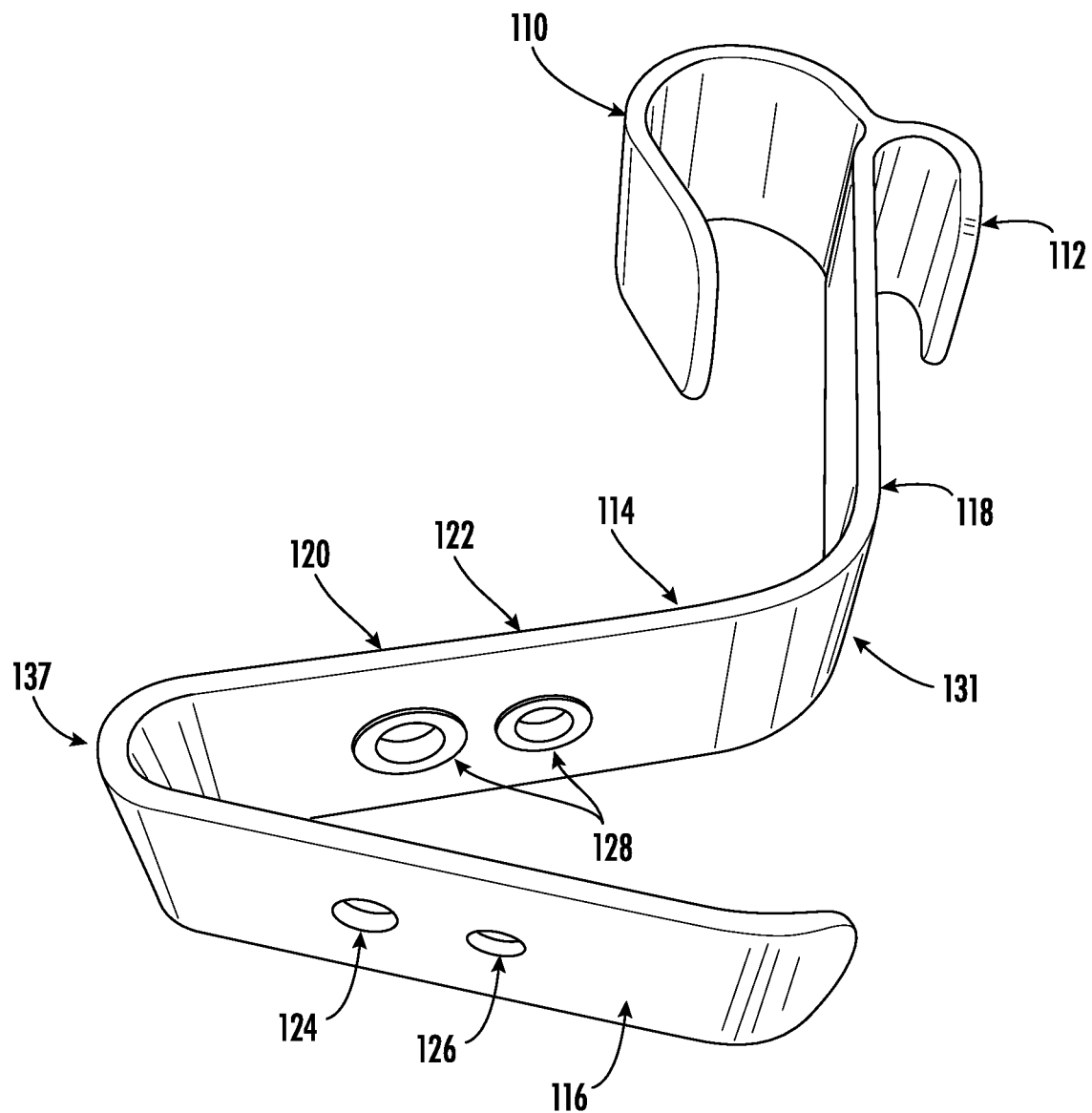
FIG. 2 is a left-side view of the invention

Turning to FIG. 2, this figure is a left-side view of the Prosthetic locking liner drying hook shown in FIG. 1. As shown in FIG. 2, on the lower surface of top grip lever 114 are 1 mm reinforced interior plastic hole openings 128, which reinforce the large and small holes 120 and 122, respectively, which receive prosthetic liner pins 130. Additionally, as illustrated in FIG. 2 are holes 124 and 126 on the lower surface of bottom grip lever 116.

Figure 3:
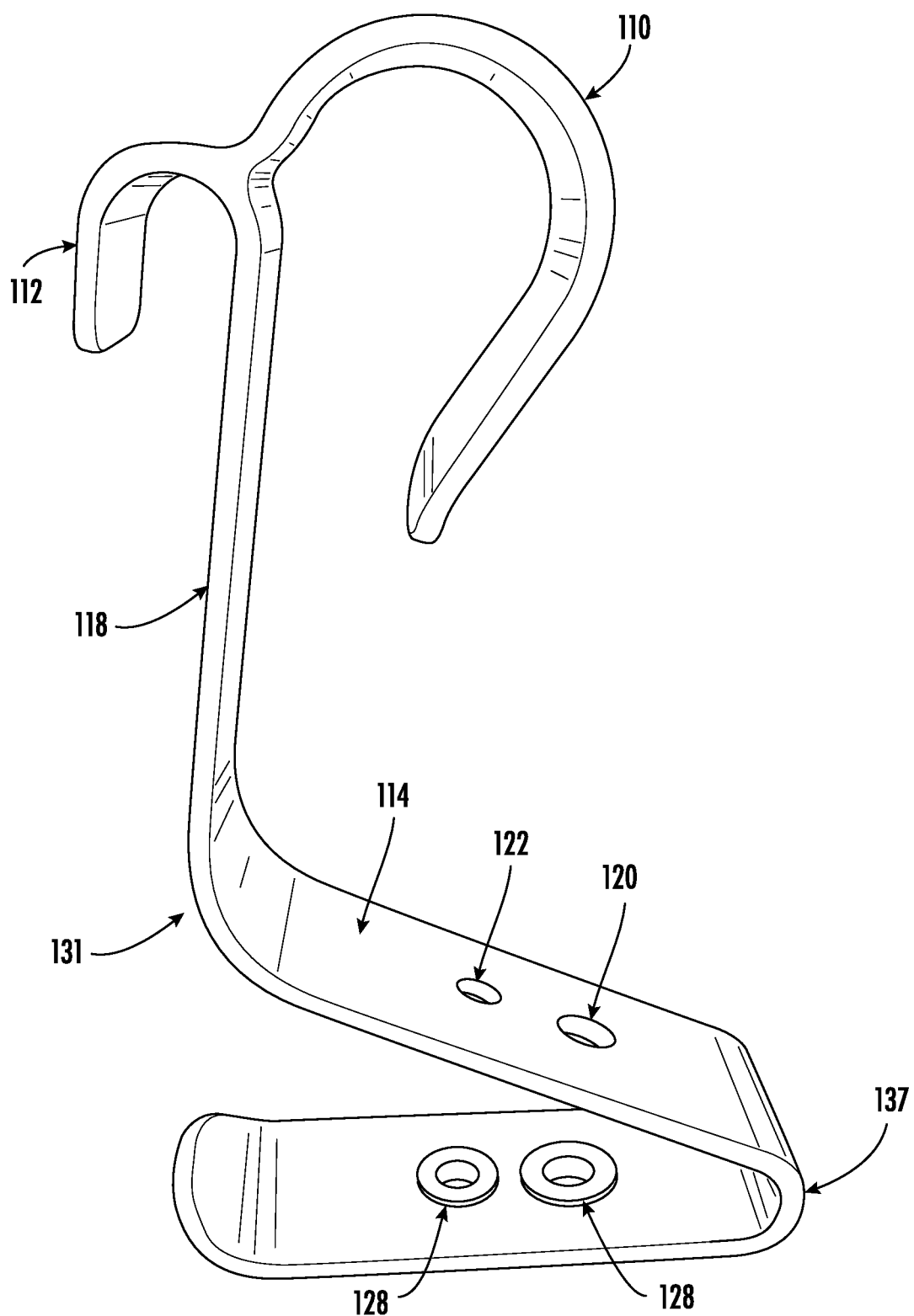
FIG. 3 is a right-side view of the invention

As shown in FIG. 3, as illustrated, is a right-side view of the prosthetic locking liner dryer hook of the invention.

Figure 4:
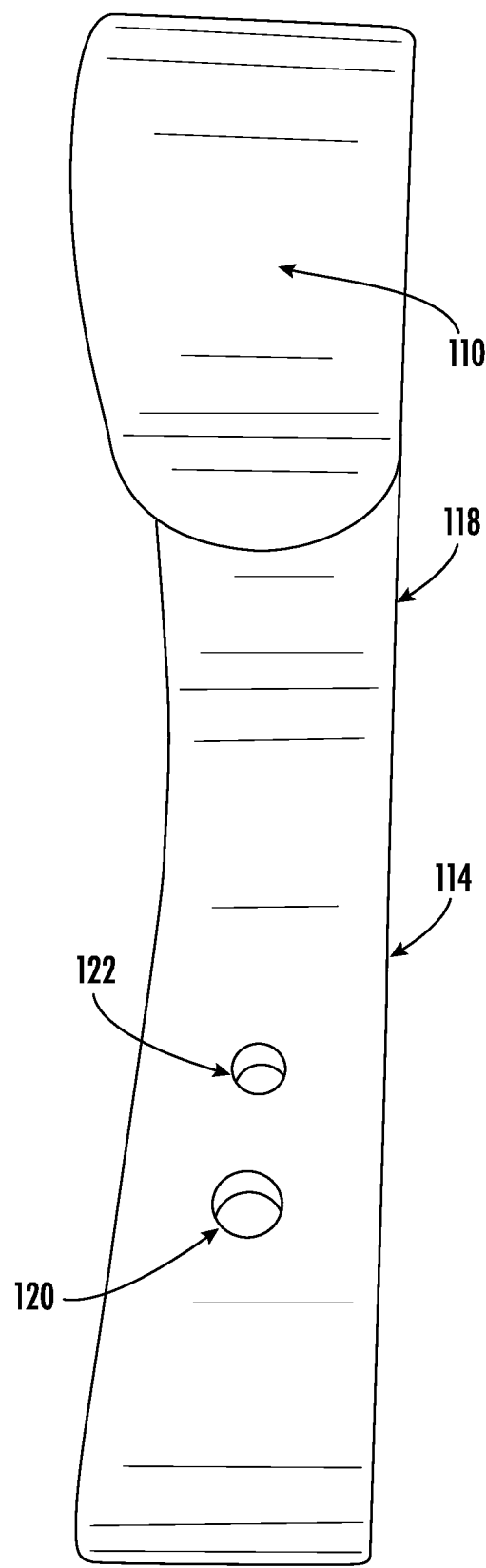
FIG. 4 is a rear view of the invention
FIG. 5 a perspective rear view of the invention
FIG. 6. Is a perspective view of the locking liner hook hanging from a shower rod.

Shown in FIG. 4 are the large hole 120 and the small hole 122 of the top grip lever 114. Although two sets of holes are shown in each of the top and bottom grip levers, more or less than two holes can be present in the grip levers and the sizes of the holes may vary. Also, although the reinforced holes 128 are shown as being on one side of each of the top and bottom grip levers, they can also be on both sides of each of the top and bottom levers or both sides of one grip lever or only on one grip lever, as would be understood by one of ordinary skill in the art.

Figure 5:
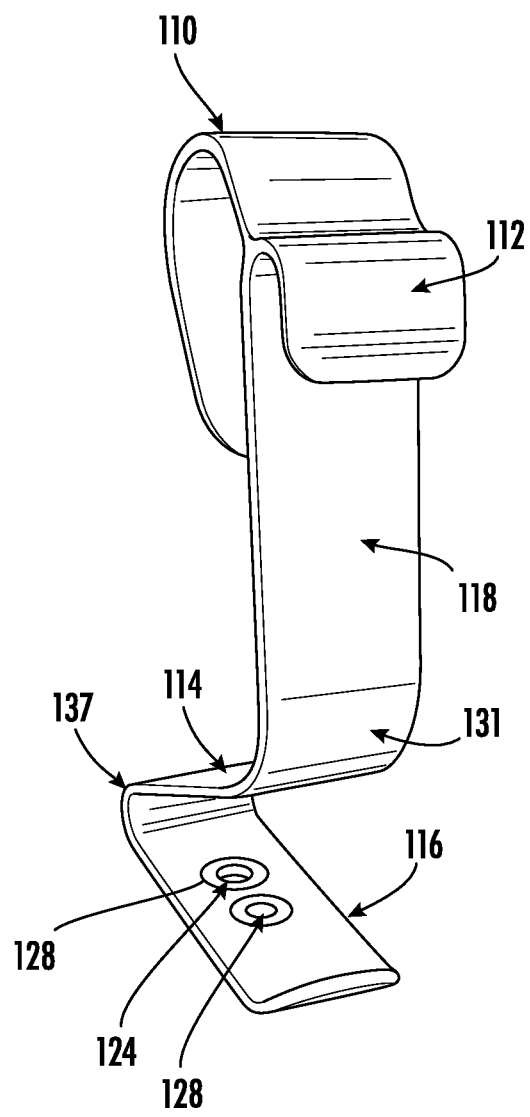

FIG. 5 illustrates the prosthetic locking liner dryer hook from a rear perspective, compared to FIG. 1.

Figure 6:
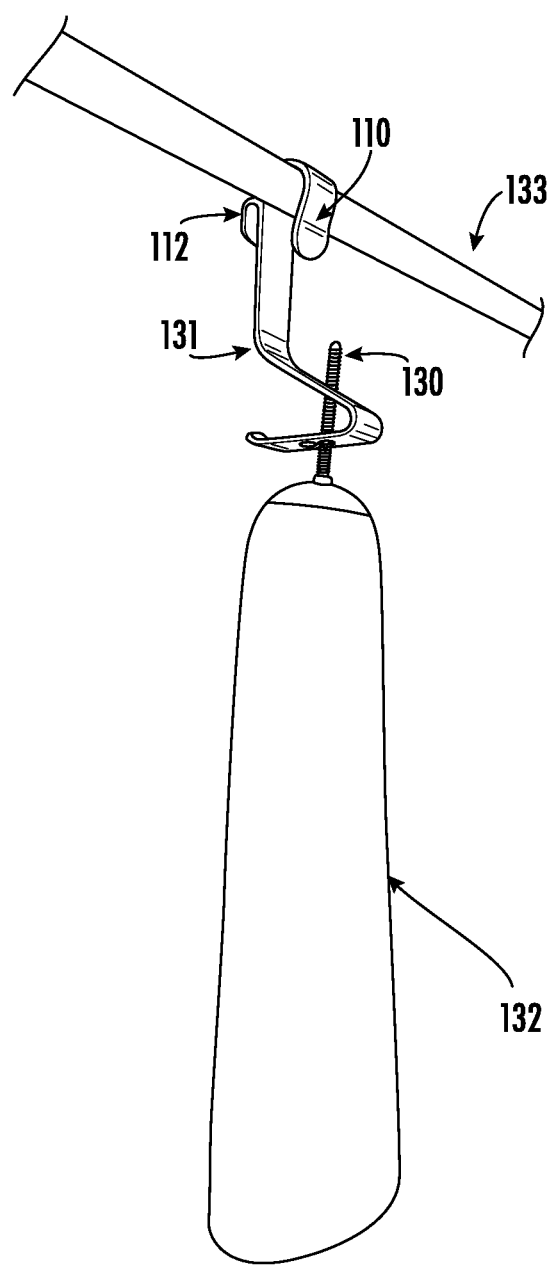

FIG. 6 illustrates a prosthetic locking liner dryer hook on a curtain rod 133. Also shown in this figure is a liner 132 connected to the prosthetic locking liner dryer hook by a prosthetic liner pin 130, which is shown to be extending upwardly through hole 120 in the top grip lever 114 and hole 124 in the bottom grip lever, as better shown in FIGS. 1 and 2.

Figure 7:
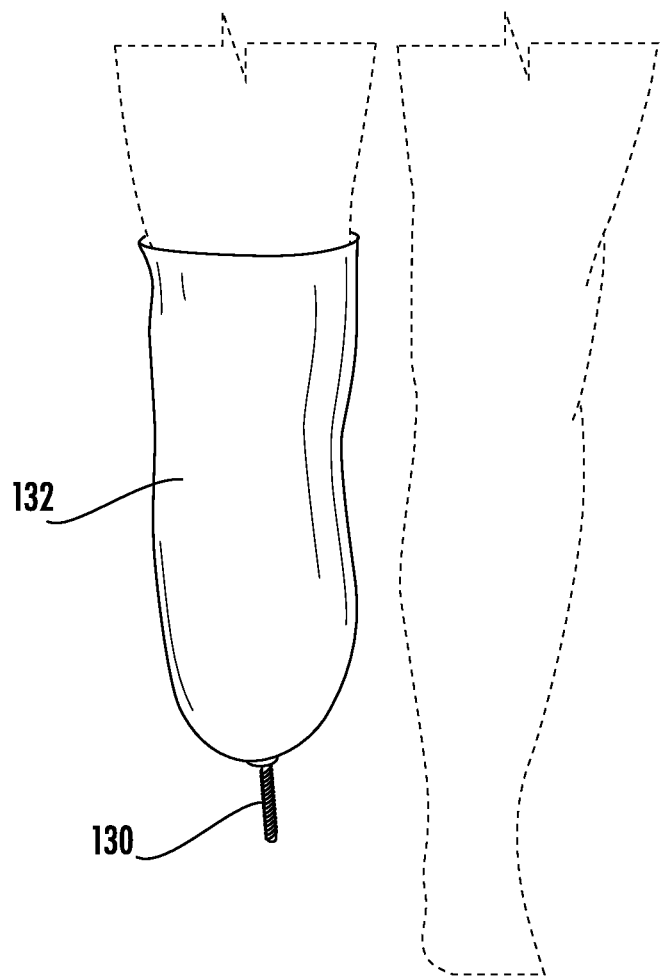
FIG. 7. Is an example of a prosthetic locking liner with a locking pin, worn by a standing amputee.

FIG. 7 illustrates an amputee wearing a prosthetic locking liner 132 with a locking pin 130 protruding therefrom, while in a standing position.

Figure 8:
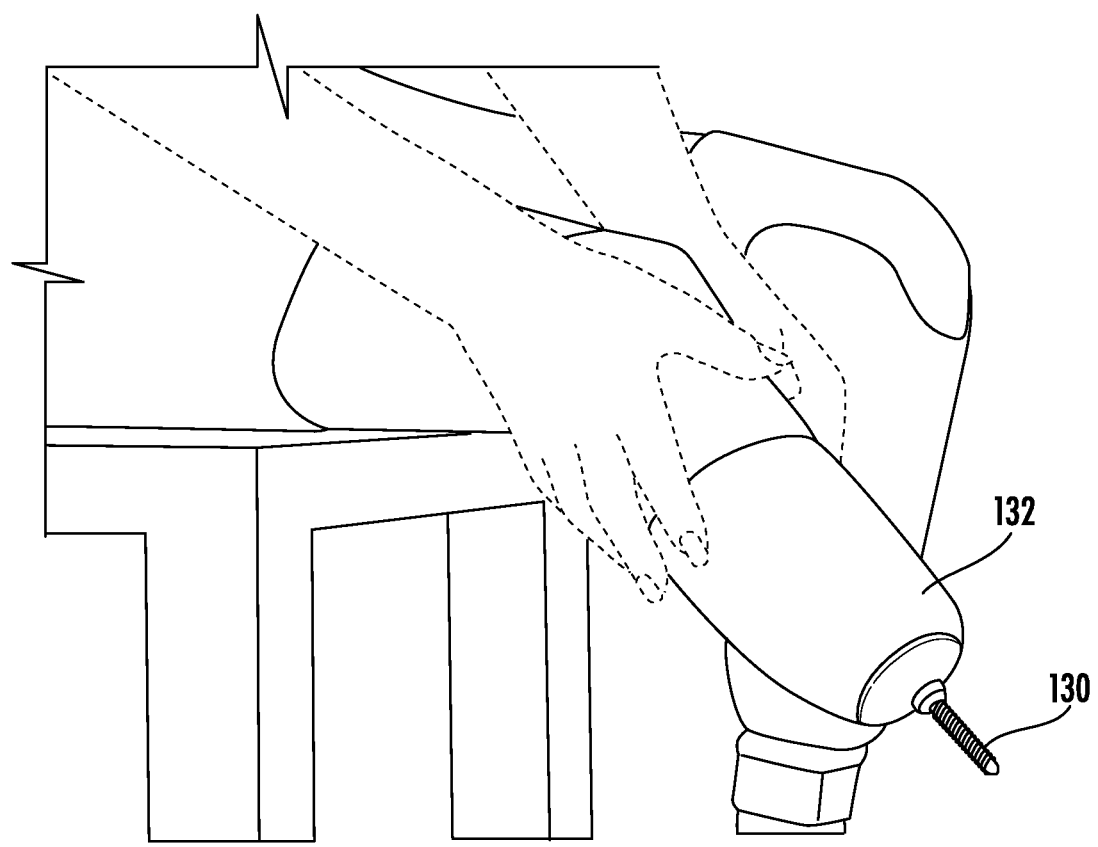
FIG. 8. Is an example of a prosthetic locking liner with a locking pin worn by a seated amputee.

FIG. 8 shows an amputee wearing a prosthetic locking liner 132 with a locking pin 130 protruding therefrom, while in a seated position.

Figure 9:
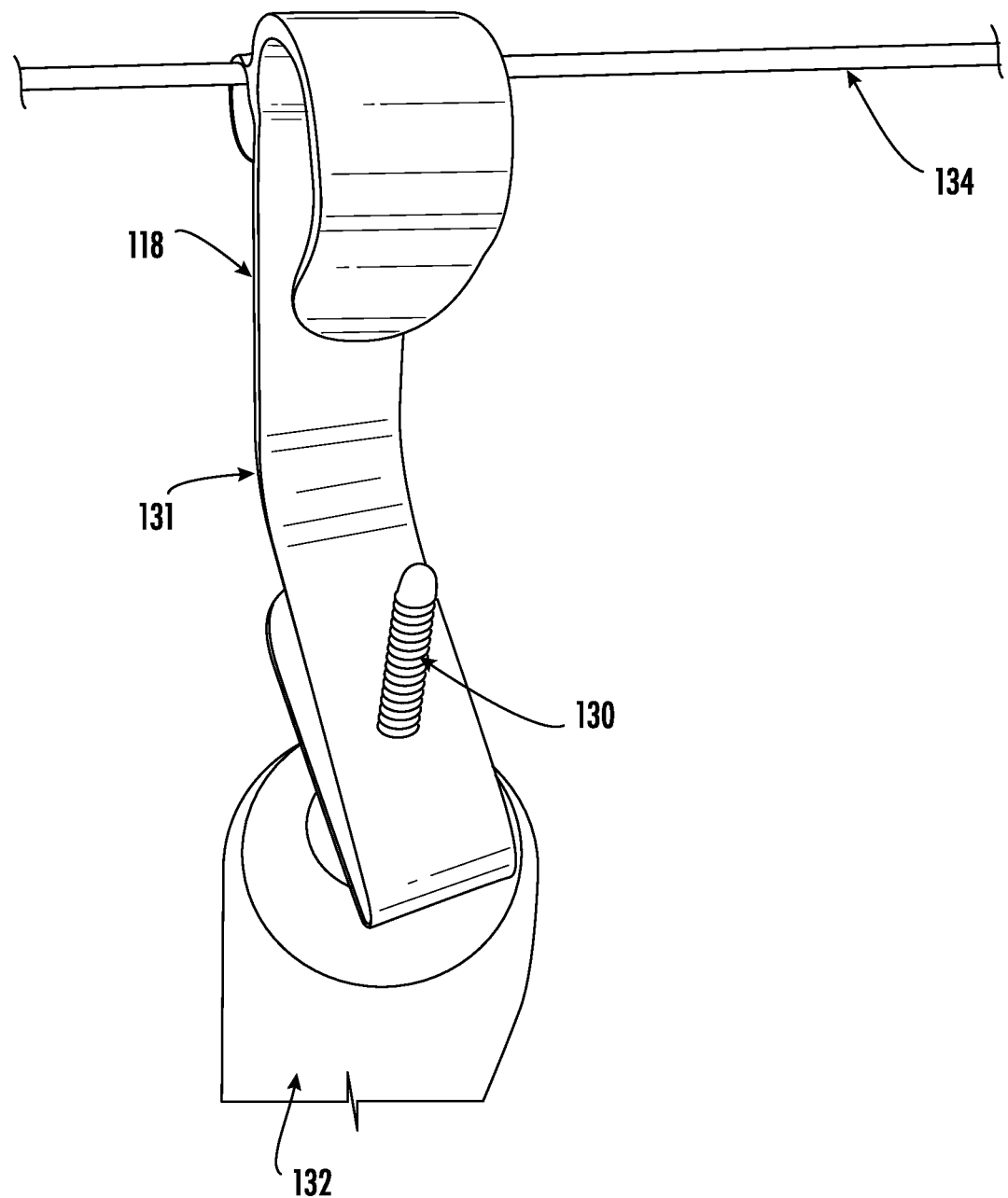
FIG. 9. Is an example of a prosthetic licking liner with a locking pin hanging from a shower door.

FIG. 9 illustrates an embodiment of the invention with a prosthetic locking liner 132 with a protruding locking pin 130. As shown, the licking pin extends through the top and bottom grip levers 114 and 116 (FIG. 1) and hangs over a shower door 134.

Figure 10:
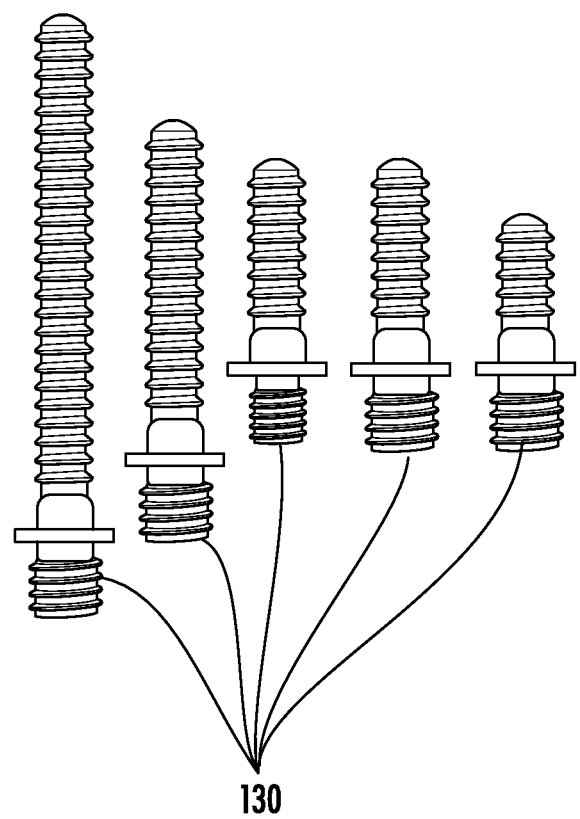
FIG. 10. Is an example of pins for locking liners.

FIG. 10 illustrates different sizes of locking pins 130 for use by different sized individuals.

In operation, once a prosthetic locking liner with a prosthetic liner pin (132 and 130, respectively) is cleaned, one squeezes together the top grip lever (114) together with the bottom grip lever (116) creating an easy entry or insertion of a prosthetic liner pin (130), that is attached to a prosthetic locking liner (132). Depending on the size and thickness of a prosthetic liner pin (130), one can determine which hole in the top and bottom grip levers has a better fit. One can either use the large holes (120 & 124) for larger and thicker liner pins, located on both the anterior section of the top grip lever (114) and bottom grip lever (116); or the posterior small holes (122 & 126) for smaller and thinner liner pins (130), located on both the posterior section of the top grip lever (114) and bottom grip lever (116). Once the prosthetic liner pin (130), that is attached to a prosthetic locking liner (132), is inserted in the appropriate size hole, one releases both the top grip lever (114) and the bottom grip lever (116). This creates a strong tension between the two grips which prevents the release of a prosthetic liner pin (130) from the holes. One can either hang the prosthetic locking liner hook on the shower curtain rod hook (110) or onto the integrated shower door clasp (112). One can also hang the prosthetic locking liner hooks 110 or 112 from any surface edge as well. To release and remove the prosthetic liner pin (130) that is attached to the prosthetic locking liner (132), one simply squeezes both the top grip lever (114) and bottom grip lever (116) at the same time and the prosthetic locking liner (132) with prosthetic line pin (130) will easily slide out. Although two grip levers are illustrated, a single or triple grip lever can also be used. The single grip lever would be at an angle as is the preferred top grip lever and if a single grip lever is used that is generally flat as is the preferred bottom grip lever, a nut or other connection mechanism would be used to keep the pin from falling through, as would be readily understood by one of ordinary skill in the art.

Although exemplary embodiments with alternative hooks 110 and 112; different sets and sizes of holes (120, 124) 122, 126); different sizes of prosthetic liner pins, and different amounts and types of grip levers, etc. have been disclosed as examples of how the invention can be carried out, other exemplary embodiments would be readily apparent to one of ordinary skill in the art. The claims should not be construed based solely upon on the disclosed exemplary embodiments, but rather on the metes and bonds of the appended claims.

What is claimed is:

1. A prosthetic locking liner drying hook, the prosthetic locking liner drying hook comprising:
    a bottom grip lever extending in a generally horizontal direction;
    a top grip lever connected to the bottom grip lever by a first curved connecting member extending from an edge of the top grip lever to an edge of the bottom grip lever;
    at least one hole extending through each of the top grip lever and the bottom grip lever forming a first set of holes;
    a second curved connecting member opposite an end from which the first curved connecting member extends or is connected to the top grip lever;
    the top grip lever being at an upward angle of between 25-40 degrees, compared to the generally horizontal bottom grip lever;
    a vertically extending plate extending upwardly from the second curved lever; and;
    at least one curtain rod hook or shower door hook projecting from the vertically extending plate; wherein the prosthetic locking liner drying hook receives a prosthetic liner pin extending through the top and bottom grip levers.

2. The prosthetic locking dryer liner of claim 1, further comprising both the at least one curtain rod hook and shower door hook projecting from the vertically extending plate.

3. The prosthetic locking dryer liner of claim 2, wherein the curtain od hook and the shower door hook extend outwardly from the vertically extending plate in different directions.

4. The prosthetic locking dryer liner of claim 3, wherein the curtain rod hook and the shower door hook extend from the vertically extending plate in directions that are opposite each other.

5. The prosthetic locking dryer liner of claim 1, further comprising a second set of holes extending through the top grip lever and the bottom grip lever; wherein the first and second holes are different sizes; which allow different sizes of prosthetic liner pins to be alternatively used.

6. The prosthetic locking dryer liner of claim 5, further comprising an upper surface of the bottom grip lever holes have 1 mm or smaller or larger reinforcing members for assisting in keeping the prosthetic liner pin in place.

7. The prosthetic locking dryer liner of claim 6, further comprising a lower surface of the top grip lever holes have 1 mm or smaller or larger reinforcing members for assisting in keeping the prosthetic liner pin in place.

8. A prosthetic locking liner drying hook, the prosthetic locking liner drying hook comprising:
    a bottom grip lever extending in a generally horizontal direction;
    a top grip lever connected to the bottom grip lever by a first curved connecting member extending from an edge of the top grip lever to an edge of the bottom grip lever;
    two holes extending through each of the top grip lever and the bottom grip lever;
    a second curved connecting member extending upwardly from the top grip lever which is opposite an end from which the first curved connecting member extends or is connected to the top grip member;
    the top grip lever being at an upward angle of between 25-40 degrees compared to the generally horizontal bottom grip lever;
    a vertically extending plate extending upwardly from the second curved connecting member; and;
    at least one curtain rod hook or shower door hook projecting from the vertically extending plate.

9. The prosthetic locking liner dryer hook of claim 8, further comprising wherein the prosthetic locking liner drying hook is configured to receive a prosthetic liner pin extending through the top and bottom grip levers.

10. The prosthetic locking liner dryer hook of claim 8, further comprising the two holes are different sizes to accommodate different size prosthetic liner pins.

11. The prosthetic locking dryer liner of claim 8, further comprising both a curtain rod hook and a shower door hook projecting from the vertically extending plate.

12. The prosthetic locking dryer liner of claim 11, wherein the curtain rod hook and the shower door hook extend outwardly from the vertically extending plate in different directions.

13. The prosthetic locking dryer liner of claim 12, wherein the curtain rod hook and the shower door hook extend in directions from the vertically extending plate that are opposite each other.

14. The prosthetic locking dryer liner of claim 8, further comprising an upper surface of the bottom grip lever holes have 1 mm or smaller or larger reinforcing members for assisting in keeping the prosthetic liner pin in place.

15. The prosthetic locking dryer liner of claim 14, further comprising a lower surface of the top grip lever have 1 mm or smaller or larger reinforcing members for assisting in keeping the prosthetic liner pin in place.

\* \* \* \* \*